US007737167B2

(12) United States Patent
Sørensen et al.

(10) Patent No.: US 7,737,167 B2
(45) Date of Patent: Jun. 15, 2010

(54) 2-AMINO BENZIMIDAZOLE DERIVATIVES AND THEIR USE AS MODULATORS OF SMALL-CONDUCTANCE CALCIUM-ACTIVATED POTASSIUM CHANNELS

(75) Inventors: Ulrik Svane Sørensen, Ballerup (DK); Lene Teuber, Ballerup (DK); Dan Peters, Ballerup (DK); Dorte Strøbæk, Ballerup (DK); Tina Holm Johansen, Ballerup (DK); Karin Sandager Nielsen, Ballerup (DK); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 306 days.

(21) Appl. No.: 11/628,970

(22) PCT Filed: Aug. 3, 2005

(86) PCT No.: PCT/EP2005/053792

§ 371 (c)(1),
(2), (4) Date: Dec. 8, 2006

(87) PCT Pub. No.: WO2006/013210

PCT Pub. Date: Feb. 9, 2006

(65) Prior Publication Data

US 2007/0197618 A1    Aug. 23, 2007

Related U.S. Application Data

(60) Provisional application No. 60/599,025, filed on Aug. 6, 2004.

(30) Foreign Application Priority Data

Aug. 5, 2004   (DK) .............................. 2004 01191

(51) Int. Cl.
*A61K 31/4184* (2006.01)
*C07D 235/04* (2006.01)

(52) U.S. Cl. .................................... 514/395; 548/307.4
(58) Field of Classification Search .................. None
See application file for complete search history.

(56) References Cited

U.S. PATENT DOCUMENTS

2009/0131503 A1 * 5/2009 Annedi et al. ............... 514/414

FOREIGN PATENT DOCUMENTS

| WO | WO-00/01676 A1 | 1/2000 |
| WO | WO-00/69838 A | 11/2000 |
| WO | WO-01/02406 A | 1/2001 |
| WO | WO-03/094861 A2 | 11/2003 |
| WO | WO-2004/035056 A | 4/2004 |

OTHER PUBLICATIONS

Parihar et al. Alzheimer's disease pathogenesis and therapeutic interventions, Journal of Clinical Neuroscience (2004) 11(5), 456-467.*
Loscher et al. Drug Resistance in Brain Diseases and the Role of Drug Efflux Transporters, Nature Reviews, vol. 6, Aug. 2005, 591-602.*
Strobek et al. Pharmacological characterization of small-conductance Ca2- activated K channels expressed in HEK293 cells, British Journal of Pharmacology (2000) 129, 991-999.*
Claudia A. Sailer et al., Mol. Cell. Neurosci. 26 (2004) pp. 458-469.
J.-F Liegeois et al., Current Medicinal Chemistry, 2003, 10, pp. 625-647.

* cited by examiner

*Primary Examiner*—Phyllis G. Spivack
(74) *Attorney, Agent, or Firm*—Birch, Stewart, Kolasch & Birch, LLP

(57) ABSTRACT

This invention relates to novel 2-amino benzimidazole derivatives useful as modulators of small-conductance calcium-activated potassium channels (SK channels).

In other aspects the invention relates to the use of these compounds in a method for therapy and to pharmaceutical compositions comprising the compounds of the invention.

11 Claims, No Drawings

2-AMINO BENZIMIDAZOLE DERIVATIVES AND THEIR USE AS MODULATORS OF SMALL-CONDUCTANCE CALCIUM-ACTIVATED POTASSIUM CHANNELS

This application is the National Phase of PCT/EP2005/053792 filed on Aug. 3, 2005, which claims priority under 35 U.S.C. 119(e) to U.S. Provisional Application No. 60/599,025 filed on Aug. 6, 2004 and under 35 U.S.C. 119(a) to Patent Application No. PA 2004 01191 filed in Denmark on Aug. 5, 2004. Both of these prior applications are hereby expressly incorporated by reference into the present application.

TECHNICAL FIELD

This invention relates to novel 2-amino benzimidazole derivatives useful as modulators of small-conductance calcium-activated potassium channels (SK channels). In other aspects the invention relates to the use of these compounds in a method for therapy and to pharmaceutical compositions comprising the compounds of the invention.

BACKGROUND ART

Three subtypes of small-conductance calcium-activated potassium channels (SK channels) have been cloned: SK1, SK2 and SK3 (corresponding to KCNN1-3 using the genomic nomenclature). The activity of these channels is determined by the concentration of free intracellular calcium ($[Ca^{2+}]_i$) via calmodulin that is constitutively bound to the channels. SK channels are tightly regulated by $[Ca^{2+}]_i$ in the physiological range being closed at $[Ca^{2+}]_i$ up to around 0.1 µM but fully activated at a $[Ca^{2+}]_i$ of 1 µM. Being selective for potassium, open or active SK channels have a hyperpolarizing influence on the membrane potential of the cell. SK channels are widely expressed in the central nervous system. The distribution of SK1 and SK2 show a high degree of overlap and display the highest levels of expression in neocortical, limbic and hippocampal areas in the mouse brain. In contrast, the SK3 channels show high levels of expression in the basal ganglia, thalamus and the brain stem monoaminergic neurons e.g. dorsal raphe, locus coeruleus and the ventral tegmental area (Sailer et al. "Comparative immunohistochemical distribution of three small-conductance $Ca^{2+}$-activated potassium channel subunits, SK1, SK2, and SK3 in mouse brain, Mol. Cell. Neurosci. 2004, 26, 458-469). The SK channels are also present in several peripheral cells including skeletal muscle, gland cells, liver cells and T-lymphocytes.

The hyperpolarizing action of active SK channels plays an important role in the control of firing pattern and excitability of excitable cells. SK channel inhibitors such as apamin and bicuculline-methobromide have been demonstrated to increase excitability whereas the opener 1-EBIO is able to reduce electrical activity. In non-excitable cells where the amount of $Ca^{2+}$ influx via voltage-independent pathways is highly sensitive to the membrane potential an activation of SK channels will increase the driving force whereas a blocker of SK channels will have a depolarising effect and thus diminish the driving force for calcium.

Based on the important role of SK channels in linking $[Ca^{2+}]_i$ and membrane potential, SK channels are an interesting target for developing novel therapeutic agents.

WO 03/094861 (Icagen Inc) describes bis-benzimidazoles and related compounds as potassium channel modulators.

A review of SK channels and SK channel modulators may be found in Liegeois, J.-F. et al.: "Modulation of small conductance calcium-activated potassium (SK) channels: a new challenge in medicinal chemistry", Current Medicinal Chemistry, 2003, 10, 625-647.

Known modulators of SK channels suffer from being large molecules or peptides (apamin, scyllatoxin, tubocurarine, dequalinium chloride, UCL1684) or having low potency (1-EBIO, riluzole). Thus, there is a continued need for compounds with an optimized pharmacological profile. In particular, there is a great need for selective ligands, such as SK3 channel modulators.

SUMMARY OF THE INVENTION

In its first aspect, the invention provides a 2-amino benzimidazole derivative of the Formula I:

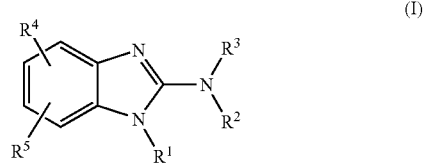

(I)

or any of its isomers or any mixture of its isomers, or a pharmaceutically acceptable salt thereof, wherein $R^1$, $R^2$, $R^3$, $R^4$ and $R^5$ are as defined below.

In its second aspect, the invention provides a pharmaceutical composition, comprising a therapeutically effective amount of a compound of the invention, or any of its isomers or any mixture of its isomers, or a pharmaceutically acceptable salt thereof, together with at least one pharmaceutically acceptable carrier, excipient or diluent.

In a further aspect, the invention provides the use of a compound of the invention, or any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of SK channels.

In a still further aspect, the invention relates to a method for treatment, prevention or alleviation of a disease or a disorder or a condition of a living animal body, including a human, which disorder, disease or condition is responsive to modulation of SK channels, which method comprises the step of administering to such a living animal body in need thereof a therapeutically effective amount of a compound of the invention, or any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION 2-amino benzimidazole derivatives

In its first aspect the present invention provides 2-amino benzimidazole derivatives of formula I:

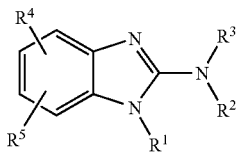
(I)

or any of its isomers or any mixture of its isomers, or a pharmaceutically acceptable salt thereof, wherein
$R^1$ represents hydrogen or alkyl;
$R^2$ represents hydrogen, alkyl or alkoxy;
$R^3$ represents a ring-containing group selected from:

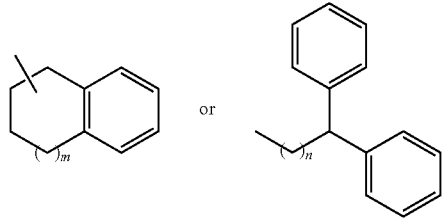

wherein
m is 0, 1 or 2;
n is 0, 1, 2, 3 or 4;
and wherein the ring(s) of $R^3$ independent of each other are optionally substituted with one or more substituents independently selected from the group consisting of:
halo, trifluoromethyl, trifluoromethoxy, cyano, alkyl and alkoxy;
$R^4$ and $R^5$ independent of each other are selected from the group consisting of:
hydrogen, halo, trifluoromethyl, trifluoromethoxy, cyano, alkyl and alkoxy.
In a special embodiment, $R^1$ represents hydrogen or alkyl; $R^2$ represents hydrogen, alkyl or alkoxy;
$R^3$ represents a ring-containing group selected from:

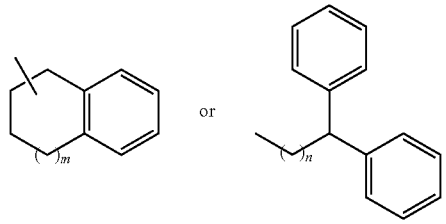

wherein
m is 0, 1 or 2;
n is 0, 1, 2, 3 or 4;
and wherein the aromatic moieties of $R^3$ independent of each other are optionally substituted with one or more substituents independently selected from the group consisting of:
halo, trifluoromethyl, trifluoromethoxy, cyano, alkyl and alkoxy;
$R^4$ and $R^5$ independent of each other are selected from the group consisting of:
hydrogen, halo, trifluoromethyl, trifluoromethoxy, cyano, alkyl and alkoxy.
In one embodiment, $R^1$ represents hydrogen.
In a second embodiment, $R^2$ represents hydrogen.

In a further embodiment, $R^3$ represents a 1,2,3,4-tetrahydro-naphthyl group, wherein the ring is optionally substituted with one or more substituents independently selected from the group consisting of: halo, trifluoromethyl, trifluoromethoxy, cyano, alkyl and alkoxy. In a special embodiment, $R^3$ represents a 1,2,3,4-tetrahydro-naphthyl group substituted with alkyl, such as 2-methyl-1,2,3,4-tetrahydro-naphtalen-1-yl or 4-methyl-1,2,3,4-tetrahydro-naphtalen-1-yl. In a further embodiment, $R^3$ represents a 1,2,3,4-tetrahydro-naphthyl group substituted twice with alkyl, such as 5,7-dimethyl-1,2,3,4-tetrahydro-naphtalen-1-yl In a further embodiment, $R^3$ represents a 1,2,3,4-tetrahydro-naphthyl group, wherein the aromatic moiety is optionally substituted with one or more substituents independently selected from the group consisting of: halo, trifluoromethyl, trifluoromethoxy, cyano, alkyl and alkoxy. In a special embodiment, $R^3$ represents a 1,2,3,4-tetrahydro-naphthyl group, such as 1,2,3,4-tetrahydro-naphtalen-1-yl. In a further embodiment, $R^3$ represents a 1,2,3,4-tetrahydro-naphthyl group substituted with halo, such as 7-halo-1,2,3,4-tetrahydro-naphtalen-1-yl, such as 7-fluoro-1,2,3,4-tetrahydro-naphtalen-1-yl or 7-chloro-1,2,3,4-tetrahydro-naphtalen-1-yl.

In a still further embodiment, $R^3$ represents an indanyl group, wherein the aromatic moiety is optionally substituted with one or more substituents independently selected from the group consisting of: halo, trifluoromethyl, trifluoromethoxy, cyano, alkyl and alkoxy. In a special embodiment, $R^3$ represents indanyl, such as indan-1-yl or indan-2-yl. In a further embodiment, $R^3$ represents indanyl substituted with halo, such as 5-halo-indan-1-yl, such as 5-bromo-indan-1-yl, 5-chloro-indan-1-yl or 5-fluoro-indan-1-yl.

In a further embodiment, $R^3$ represents a 6,7,8,9-tetrahydro-5H-benzocycloheptenyl group, wherein the ring is optionally substituted with one or more substituents independently selected from the group consisting of: halo, trifluoromethyl, trifluoromethoxy, cyano, alkyl and alkoxy. In a special embodiment, $R^3$ represents a 6,7,8,9-tetrahydro-5H-benzocycloheptenyl group, such as 6,7,8,9-tetrahydro-5H-benzocycloheptenyl-5-yl.

In a further embodiment, $R^3$ represents

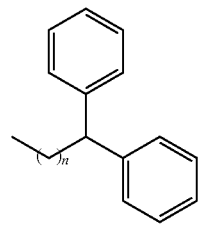

wherein the two phenyl rings independent of each other are optionally substituted with one or more substituents independently selected from the group consisting of: halo, trifluoromethyl, trifluoromethoxy, cyano, alkyl and alkoxy. In a special embodiment, $R^3$ represents diphenylmethyl (in the following named benzhydryl). In a further embodiment, $R^3$ represents 2,2-diphenylethyl. In a still further embodiment, $R^3$ represents 3,3-diphenylpropyl.

In a further embodiment, R³ represents

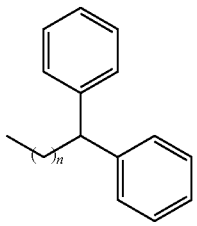

wherein the two phenyl rings independent of each other are optionally substituted with one or more halo, such as chloro or fluoro. In a special embodiment, R³ represents 4-halobenzhydryl, such as 4-chlorobenzhydryl. In a further embodiment, R³ represents 4,4'-dihalobenzhydryl, such as 4,4'-difluorobenzhydryl. In a still further embodiment, R³ represents 2,2-bis(4-halophenyl)ethyl, such as 2,2-bis(4-chlorophenyl)ethyl or 2,2-bis(4-fluorophenyl)ethyl.

In a further embodiment, n is 0, 1 or 2. In one embodiment, n is 0. In a second embodiment, n is 1. In a third embodiment, n is 2.

In a still further embodiment, m is 0. In a second embodiment, m is 1. In a third embodiment, m is 2.

In a still further embodiment, R⁴ and R⁵ represent hydrogen. In a further embodiment, R⁴ represents hydrogen and R⁵ represents alkyl, such as methyl. In a still further embodiment, R⁴ represents alkyl, such as methyl, and R⁵ represents alkyl, such as methyl. In a further embodiment, R⁴ represents hydrogen and R⁵ represents halo, such as fluoro. In a still further embodiment, R⁴ represents trifluoromethyl and R⁵ represents trifluoromethyl.

In a further embodiment, the compound of formula I, is a benzimidazole derivative substituted with one of R⁴ or R⁵ at the 5-position of the benzimidazole ring and substituted with the other of R⁴ or R⁵ at the 6-position of the benzimidazole ring. In a still further embodiment, the compound of formula I, is a benzimidazole derivative substituted with one of R⁴ or R⁵ at the 5-position of the benzimidazole ring and substituted with the other of R⁴ or R⁵ at the 7-position of the benzimidazole ring.

In a special embodiment the chemical compound of the invention is

N-(Benzimidazol-2-yl)-2,2-diphenylethylamine;
N-(Benzimidazol-2-yl)-2,2-bis(4-fluorophenyl)ethylamine;
N-(Benzimidazol-2-yl)-2,2-bis(4-chlorophenyl)ethylamine;
N-(Benzimidazol-2-yl)-3,3-diphenylpropylamine;
N-(Benzimidazol-2-yl)-1-indanylamine;
N-(Benzimidazol-2-yl)-2-indanylamine;
N-(Benzimidazol-2-yl)-5-fluoro-1-indanylamine;
N-(Benzimidazol-2-yl)-5-chloro-1-indanylamine;
N-(Benzimidazol-2-yl)-5-bromo-1-indanylamine;
N-(Benzimidazol-2-yl)-1,2,3,4-tetrahydro-1-naphtylamine;
N-(Benzimidazol-2-yl)benzhydrylamine;
N-(Benzimidazol-2-yl)-4-chlorobenzhydrylamine;
N-(Benzimidazol-2-yl)-4,4'-dichlorobenzhydrylamine;
N-(Benzimidazol-2-yl)-4,4'-difluorobenzhydrylamine;
N-(Benzimidazol-2-yl)-6,7,8,9-tetrahydro-5H-benzocyclohepten-5-ylamine;
(R)-N-(Benzimidazol-2-yl)-1,2,3,4-tetrahydro-1-naphthylamine;
(S)-N-(Benzimidazol-2-yl)-1,2,3,4-tetrahydro-1-naphthylamine;
N-(Benzimidazol-2-yl)-2-methyl-1,2,3,4-tetrahydro-1-naphthylamine;
N-(Benzimidazol-2-yl)-5,7-dimethyl-1,2,3,4-tetrahydro-1-naphthylamine;
N-(Benzimidazol-2-yl)-4-methyl-1,2,3,4-tetrahydro-1-naphthylamine;
N-[5,7-Bis(trifluoromethyl)benzimidazol-2-yl]-1,2,3,4-tetrahydro-1-naphthylamine;
(R)-N-(5-Methylbenzimidazol-2-yl-1,2,3,4-tetrahydro-1-naphthylamine;
(R)-N-(5,6-Dimethylbenzimidazol-2-yl)-1,2,3,4-tetrahydro-1-naphthylamine;
N-(5-Fluorobenzimidazol-2-yl)-1,2,3,4-tetrahydro-1-naphthylamine;
N-(Benzimidazol-2-yl)-7-chloro-1,2,3,4-tetrahydro-1-naphthylamine;
N-(Benzimidazol-2-yl)-7-fluoro-1,2,3,4-tetrahydro-1-naphthylamine;

or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contains from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

Alkoxy is O-alkyl, wherein alkyl is as defined above.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centers, and that such compounds exist in the form of isomers.

Moreover, the chemical compounds of the present invention may exist as enantiomers in (+) and (−) forms as well as in racemic forms (±). The racemates of these isomers and the individual isomers themselves are within the scope of the present invention.

The invention includes all such isomers and any mixtures thereof including racemic mixtures.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *Enantiomers, Racemates, and Resolutions*", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to modulate SK channels in vitro. Functional modulation can be determined by measuring the compound-induced change in SK current by the patch clamp technique as described in Strøbaek et al.: "Pharmacological characterization of small-conductance Ca$^{2+}$-activated K channels expressed in HEK293 cells", British Journal of Pharmacology (2000) 129, 991-999. From this type of measurements the potency of a given compound can be determined as e.g. $K_i$ or $IC_{50}$ values for blockers/inhibitors and $EC_{50}$ values for openers/activators. Similar data can be obtained from other patch clamp configurations and from channels expressed endogenously in various cell lines.

In one embodiment, the compounds of the invention show selectivity for SK3 over SK1 and SK2. In a further embodiment, the compounds of the invention are positive SK channel modulators, such as positive SK3 channel modulators. In a still further embodiment, the compounds of the invention are negative modulators, such as negative SK3 channel modulators. In a special embodiment, the compounds of the invention are SK channel blockers, such as SK3 channel blockers.

Based on the activity observed in the patch clamp experiments, the compound of the invention is considered useful for the treatment, prevention or alleviation of a disease or a disorder or a condition Of a mammal, including a human, which disease, disorder or condition is responsive to modulation of SK channels.

In a special embodiment, the compounds of the invention are considered useful for the treatment, prevention or alleviation of: absence seizures, agerelated memory loss, Alzheimer's disease, angina pectoris, arrhythmia, asthma, anxiety, ataxia, attention deficits, baldness, bipolar disorder, bladder hyperexcitability, bladder outflow obstruction, bladder spasms, brain tumors, cerebral ischaemia, chronic obstructive pulmonary disease, cancer, cardiovascular disorders, cognitive dysfunction, colitis, constipation, convulsions, coronary artery spasms, coronary hearth disease, cystic fibrosis, dementia, depression, diabetes type II, dysmenorrhoea, epilepsy, gastrointestinal dysfunction, gastroesophageal reflux disorder, gastrointestinal hypomotility disorders gastrointestinal motility insufficiency, hearing loss, hyperinsulinemia, hypertension, immune suppression, inflammatory bowel disease, inflammatory pain, intermittent claudication, irritable bowel syndrome, ischaemia, ischaemic hearth disease, learning deficiencies, male erectile dysfunction, manic depression, memory deficits, migraine, mood disorders, motor neuron diseases, myokymia, myotonic dystrophy, myotonic muscle dystrophia, narcolepsy, neuropathic pain, pain, Parkinson's disease, polycystic kidney disease, postoperative ileus, premature labour, psychosis, psychotic disorders, renal disorders, Reynaud's disease, rhinorrhoea, secretory diarrhoea, seizures, Sjorgren's syndrome, sleep apnea, spasticity, sleeping disorders, stroke, traumatic brain injury, trigeminal neuralgia, urinary incontinence, urinogenital disorders, vascular spasms, vision loss, and xerostomia.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself; or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of SK channels, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: The procedures represent generic procedures used to prepare compounds of the invention. Abbreviations used are as follows:
Ac: acetyl
DMSO: dimethylsulfoxide
Et: ethyl
mp: melting point
MW: microwave
rt: room temperature
THF: tetrahydrofurane Procedure A 2-Chlorobenzimidazole and the required amine (commercially available or prepared via Procedure B) were suspended in acetonitrile in a closed vial and heated to 150-200° C. for 15-30 min by use of microwave (MW) irradiation. After cooling to rt the precipitated solid was filtered off and recrystallised from a mixture of $CH_3CN$/MeOH to give the desired product as a HCl salt. Alternatively, the precipitate from the reaction mixture was purified by column chromatography or by preparative LCMS to give the desired N-substituted 2-aminobenzimidazole as the parent compound.

An example of Procedure A, the preparation of N-(benzimidazol-2-yl)-2,2-bis(4-chlorophenyl)ethylamine, is shown in Scheme 1.

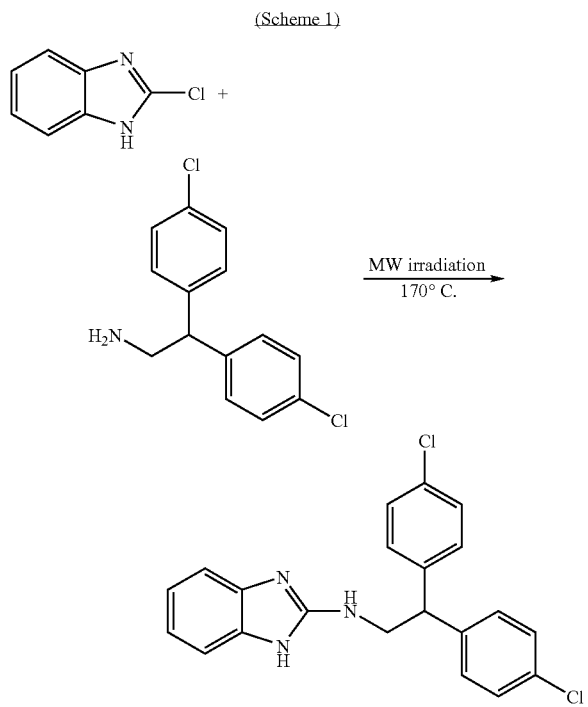

Procedure B

To a solution of the ketone or aldehyde in MeOH was added O-methylhydroxylamine HCl and stirred at rt overnight. Water was added and the mixture extracted with EtOAc. The combined organic phases were dried ($MgSO_4$), filtered and concentrated in vacuo. The crude oxime was dissolved in dry THF and added dropwise a solution of borane in THF. After stirring for 30 min under $N_2$ at rt, the reaction mixture was heated to 60° C. and stirred overnight followed by cooling to rt. Aqueous 1M NaOH was added and the mixture heated for 1 h at 60° C. Aqueous $NaHCO_3$ was added and the solution extracted with EtOAc. The combined organic phases were dried ($MgSO_4$), filtered and concentrated in vacuo to give the desired amine to be used as described in Procedure A. This amine was either used without purification or purified by column chromatography.

An example of Procedure B, the preparation of 2,2-bis(4-chlorophenyl)-ethylamine, is shown the Scheme 2.

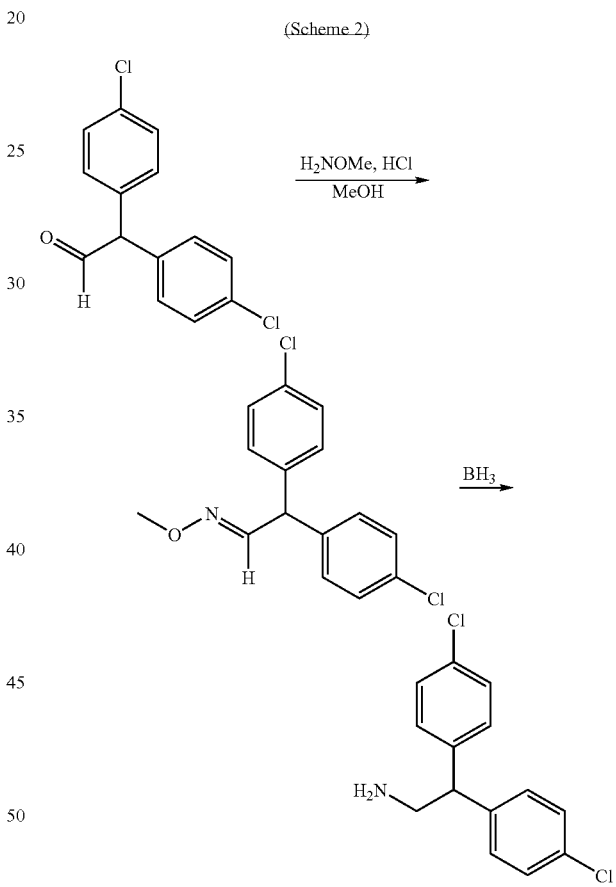

Procedure C

To a solution of 2-aminobenzimidazole and the respective aldehyde in $CH_3CN$ was added sodium triacetoxyborohydride and a catalytic amount of AcOH. The reaction mixture was heated by means of MW irradiation at 100° C. for 30 min. Aqueous $NaHCO_3$ was added, the mixture stirred and extracted with EtOAc. The combined organic phases were dried ($MgSO_4$), filtered, concentrated in vacuo and purified by preparative LCMS to give the desired N-substituted 2-aminobenzimidazole as the parent compound.

An example of Procedure C, the preparation of N-(benzimidazol-2-yl)-2,2-diphenylethylamine, is shown in Scheme 3.

(Scheme 3)

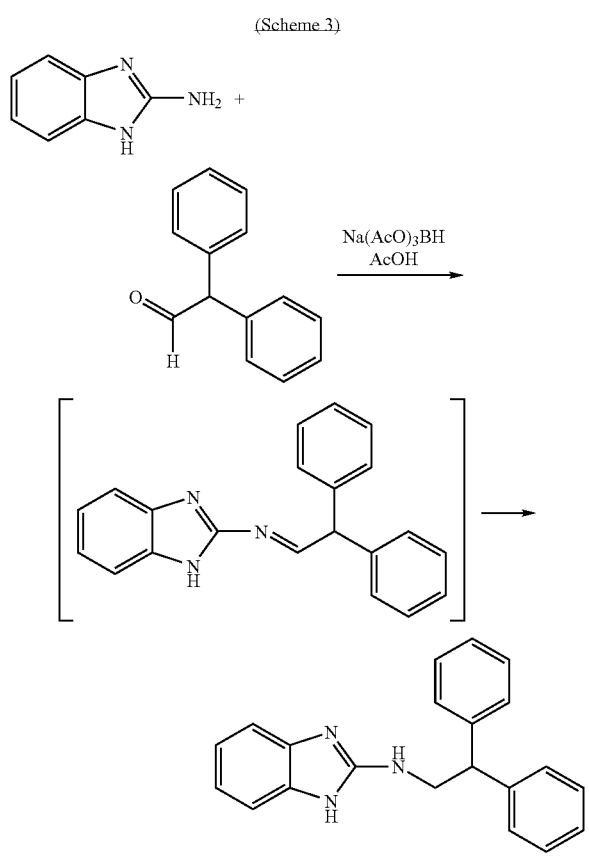

Procedure D

A mixture of an isothiocyanate (prepared by reacting the corresponding amine with thiophosgene) and a suitably substituted phenylenediamine in dry dichloromethane was stirred at rt overnight and evaporated to dryness. The resulting thiourea was then purified by e.g. column chromatography or reacted further as crude material. Thus, the thiourea was dissolved in THF, added a coupling reagent such as dicyclohexylcarbodiimide (DCC), and stirred at reflux temperature overnight. Aqueous NaHCO$_3$ was added and the solution extracted with EtOAc. The combined organic phases were dried (MgSO$_4$), filtered and concentrated in vacuo to give the crude 2-aminobenzimidazole which was subsequently purified by column chromatography or preparative LCMS.

An example of Procedure D, the preparation of N-[5,7-bis (trifluoromethyl)benzimidazol-2-yl]-1,2,3,4-tetrahydro -1-naphthylamine is shown in Scheme 4.

(Scheme 4)

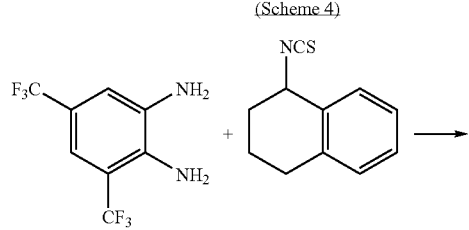

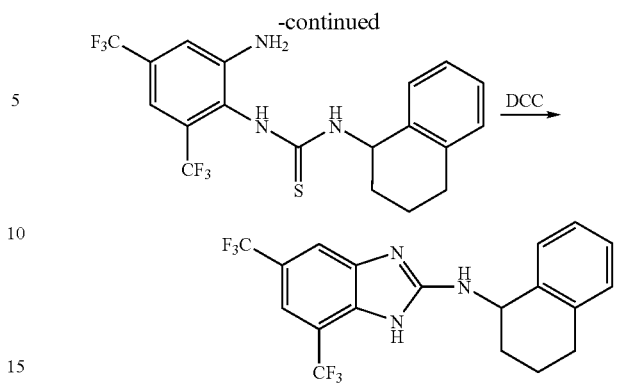

Example 1

N-(Benzimidazol-2-yl)-2,2-diphenylethylamine

The title compound was prepared from 2-aminobenzimidazole and 2,2-diphenyl-acetaldehyde by Procedure C or alternatively from 2-chlorobenzimidazole and 2,2-diphenylethylamine by Procedure A. In the latter case, the crude product was purified by recrystallisation from EtOAc/MeOH and isolated as the HCl salt (white solid, mp 153.5-154.5° C.). MS(ES$^+$) m/z 314 ([M+1]$^+$, 100). $^1$NMR (DMSO-d6) δ 4.14 (m, 2H), 4.39 (t, 1H), 7.18-7.44 (m, 14H), 9.00 (m, 1H), 12.7 (br s, 1H).

Example 2

N-(Benzimidazol-2-yl)-2,2-bis(4-fluorophenyl)ethylamine

The title compound was prepared from 2-chlorobenzimidazole and 2,2-bis(4-fluorophenyl)ethylamine (prepared by Procedure B from 2,2-bis(4-fluoro-phenyl)acetaldehyde) by Procedure A (20 min at 170° C.). The product was isolated by preparative LCMS to give the title compound as the free base (white solid, mp 155-157° C.). MS(ES$^+$) m/z 350 ([M+1]$^+$, 100) $^1$NMR (DMSO-d6) δ 3.90 (m, 2H), 4.46 (t, 1H), 6.50 (m, 1H), 6.80-6.90 (m, 2H), 7.07-7.18 (m, 6H), 7.35-7.42 (m, 4H), 10.5 (s, 1H).

Example 3

N-(Benzimidazol-2-yl)-2,2-bis(4-chlorophenyl)ethylamine

The title compound was prepared from 2-chlorobenzimidazole and 2,2-bis(4-chlorophenyl)ethylamine (prepared by Procedure B from 2,2-bis(4-chloro-phenyl)acetaldehyde) by Procedure A (20 min at 170° C.). The product was isolated by preparative LCMS to give the title compound as the free base (white solid, mp 189-190° C.). MS(ES$^+$) m/z 382 ([M+1]$^+$, 100). $^1$NMR (DMSO-d6) δ 3.91 (m, 2H), 4.47 (t, 1H), 6.52 (m, 1H), 6.81-6.90 (m, 2H), 7.06-7.18 (m, 2H), 7.33-7.36 (m, 8H), 10.6 (s, 1 H).

Example 4

N-(Benzimidazol-2-yl)-3,3-diphenylpropylamine

The title compound was prepared from 2-chlorobenzimidazole and 3,3-diphenyl-propylamine by Procedure A. The reaction mixture was added dilute aqueous HCl and CH$_2$Cl$_2$. From the CH$_2$Cl$_2$ phase a precipitate was isolated by filtration yielding the title compound in pure form as its HCl salt (mp 136.5-137.5° C.). MS(ES+) m/z 328 ([M+1]+, 100). ¹NMR (DMSO-d6) δ 2.43 (m, 2H), 3.28 (m, 2H), 4.15 (t, 1H), 7.15-7.35 (m, 14H), 9.00 (m, 1H), 12.7 (br s, 1H).

Example 5

N-(Benzimidazol-2-yl)-indanylamine

The title compound was prepared from 2-chlorobenzimidazole and racemic 1-aminoindane by Procedure A (15 min at 200° C.). The product was isolated by preparative LCMS to give the title compound as the free base and as a mixture of enantiomers (white solid, mp 195.5-197° C.). MS(ES+) m/z 250 ([M+1]+, 100). ¹NMR (DMSO-d6) δ 1.90 (m, 1 H), 2.55 (m, 1 H), 2.83 (m, 1 H), 2.95 (m, 1 H), 5.36 (m, 1 H), 6.82-6.97 (m, 3H), 7.11-7.31 (m, 6H), 10.70 (s, 1H).

Example 6

N-(Benzimidazol-2-yl)-2-indanylamine

The title compound was prepared from 2-chlorobenzimidazole and 2-aminoindane by Procedure A (15 min at 150° C.). The product was isolated by preparative LCMS to give the title compound as the free base (white solid, mp 246-249° C.). MS(ES+) m/z 250 ([M+1]+, 100). ¹NMR (DMSO-d6) δ 2.91 (dd, 2H), 3.29 (dd, 2H), 4.35 (m, 1H), 6.80-6.92 (m, 3H), 7.10-7.17 (m, 4H), 7.22-7.25 (m, 2H), 10.60 (s, 1H).

Example 7

N-(Benzimidazol-2-yl)-5-fluoro-1-indanylamine

The title compound was prepared from 2-chlorobenzimidazole and racemic 1-amino-5-bromoindane (prepared by Procedure B from 5-fluoro-1-indanone) by Procedure A (30 min at 170° C.). The product was isolated by preparative LCMS to give the title compound as the free base and as a mixture of enantiomers (white solid, mp 207-208° C.). MS(ES+) m/z 268 ([M+1]+, 100). ¹NMR (DMSO-d6) δ 1.93 (m, 1H), 2.55 (m, 1H), 2.82 (m, 1H), 2.97 (m, 1H), 5.32 (m, 1H), 6.80-6.99 (m, 4H), 7.05-7.15 (m, 3H), 7.26-7.30 (m, 1H), 10.7 (s, 1H).

Example 8

N-(Benzimidazol-2-yl)-5-chloro-1-indanylamine

The title compound was prepared from 2-chlorobenzimidazole and racemic 1-amino-5-chloroindane (prepared by Procedure B from 5-chloro-1-indanone) by Procedure A (30 min at 170° C.). The product was isolated by preparative LCMS to give the title compound as the free base and as a mixture of enantiomers (white solid, mp 242-243° C.). MS(ES+) m/z 284 ([M+1]+, 100). ¹NMR (DMSO-d6) δ 1.92 (m, 1H), 2.55 (m, 1H), 2.83 (m, 1H), 2.95 (m, 1H), 5.32 (m, 1H), 6.81-6.97 (m, 3H), 7.10-7.21 (m, 3H), 10 7.26-7.33 (m, 2H), 10.8 (s, 1H).

Example 9

N-(Benzimidazol-2-yl)-5-bromo-1-indanylamine

The title compound was prepared from 2-chlorobenzimidazole and racemic 1-amino-5-bromoindane (prepared by Procedure B from 5-bromo-1-indanone) by Procedure A (30 min at 170° C.). The product was isolated by preparative LCMS to give the title compound as the free base and as a mixture of enantiomers (white solid, mp 242-243° C.). MS(ES+) m/z 328 ([M+1]+, 100). ¹NMR (DMSO-d6) δ 1.92 (m, 1H), 2.50 (m, 1H), 2.83 (m, 1H), 2.95 (m, 1H), 5.35 (m, 1H), 6.82-7.02 (m, 3H), 7.12-7.35 (m, 4H), 7.46 (s, 1H), 10.7 (s, 1H).

Example 10

N-(Benzimidazol-2-yl)-1,2,3,4-tetrahydro-1-naphthylamine

The title compound was prepared from 2-chlorobenzimidazole and racemic 1,2,3,4-tetrahydro-l-naphthylamine by Procedure A (10 min at 170° C. followed by 15 min at 200° C.). The product was isolated from the crude reaction mixture by preparative LCMS to give the title compound as the free base and as a mixture of enantiomers (white solid, mp 230-234° C.). MS(ES+) m/z 264 ([M+1]+, 100). ¹NMR (DMSO-d6) δ 1.73-1.82 (m, 1H), 1.85-1.96 (m, 2H), 2.01-2.09 (m, 1H), 2.70-2.85 (m, 2H), 5.04 (m, 1H), 7.01-7.05 (m, 2H), 7.12-7.28 (m, 5H), 7.33-7.37 (m, 1H), 8.05 (br s, 1H).

Example 11

N-(Benzimidazol-2-yl)benzhydrylamine

The title compound was prepared from 2-chlorobenzimidazole and benzhydrylamine by Procedure A. The product was isolated by preparative LCMS to give the title compound as the free base (white solid, mp 255-258° C.). MS(ES+) m/z 300 ([M+1]+, 100). ¹NMR (DMSO-d6) δ 6.20 (d, 1H), 6.75-7.65 (m, 15H), 10.5 (s, 1H).

Example 12

N-(Benzimidazol-2-yl)-4-chlorobenzhydrylamine

The title compound was prepared from 2-chlorobenzimidazole and 4-chlorobenzhydrylamine HCl by Procedure A. The product was isolated by preparative LCMS to give the title compound as the free base (white solid, mp 180-184° C.). MS(ES+)m/z 334 ([M+1]+, 100). ¹NMR (DMSO-d6) δ 6.18 (d, 1H), 6.80-6.90 (m, 2H), 7.08-7.14 (m, 2H), 7.20-7.40 (m, 9H), 7.66 (d, 1 H), 10.6 (s, 1 H).

Example 13

N-(Benzimidazol-2-yl)-4,4'-dichlorobenzhydrylamine

The title compound was prepared from 2-chlorobenzimidazole and 4,4'-dichlorobenzhydrylamine (prepared by Procedure B from 4,4'-dichlorobenzophenone) by Procedure A. The product was isolated by preparative LCMS to give the title compound as the free base (white solid, mp 176-180° C.). MS(ES+) m/z 368 ([M+1]+, 100). ¹NMR (DMSO-d6) δ6.19 (d, 1H), 6.82-6.90 (m, 2H), 7.10-7.16 (m, 2H), 7.40 (s, 8H), 7.69 (d, 1H), 10.6 (s, 1H).

Example 14

N-(Benzimidazol-2-yl)-4,4'-difluorobenzhydrylamine

The title compound was prepared from 2-chlorobenzimidazole and 4,4'-difluoro-benzhydrylamine (prepared by Procedure B from 4,4'-difluorobenzophenone) by Procedure A. The product was isolated by preparative LCMS to give the title compound as the free base (white solid, mp 241-243° C.). MS(ES+) m/z 336 ([M+1]+, 100). ¹NMR (DMSO-d6) δ 6.20 (d, 1H), 6.80-6.91 (m, 2H), 7.09-7.20 (m, 6H), 7.38-7.43 (m, 4H), 7.69 (d, 1H), 10.6 (s, 1H).

Example 15

N-(Benzimidazol-2-yl)- 6,7,8,9-tetrahydro-5H-benzocyclohepten-5-ylamine

The title compound was prepared from 2-chlorobenzimidazole and racemic 6,7,8,9-tetrahydro-5H-benzocyclohepten-5-ylamine (prepared by Procedure B from 1-benzosuberone) by Procedure A (reflux in toluene for 2 days). The product was isolated from the reaction mixture by preparative LCMS to give the title compound as the free base and as a mixture of enantiomers (white solid, mp 203-205° C.). MS(ES$^+$) m/z 278 ([M+1]$^+$, 100). $^1$NMR (DMSO-d6) δ 1.28-1.39 (m, 1H), 1.65-2.02 (m, 5H), 2.83-2.97 (m, 2H), 5.03 (t, 1H), 6.77-6.89 (m, 2H), 7.05-7.29 (m, 7H), 10.6 (s, 1H).

Example 16

(R)-N-(Benzimidazol-2-yl)-1,2,3,4-tetrahydro-1-naphthylamine

The title compound was prepared from 2-chlorobenzimidazole and (R)-1,2,3,4-tetrahydro-l-naphthylamine by Procedure A (40 min at 170° C.). The product was filtered off and washed with acetonitrile to give the title compound as a HCl salt (white solid, mp 264-265° C.). MS(ES$^+$) m/z 264 ([M+1]$^{30}$, 100).

Example 17

(S)-N-(Benzimidazol-2-yl)-1,2,3,4-tetrahydro-1-naphthylamine

The title compound was prepared from 2-chlorobenzimidazole and (S)-1,2,3,4-tetrahydro-1-naphthylamine by Procedure A (reflux in toluene for 2 days). The product was purified by preparative LCMS, added HCl and isolated as a HCl salt (white solid, mp 257-258° C.). MS(ES$^+$) m/z 264 ([M+1]$^+$, 100).

Example 18

N-(Benzimidazol-2-yl)-2-methyl-1,2,3,4-tetrahydro-1-naphthylamine

The title compound was prepared from 2-chlorobenzimidazole and 2 methyl 1,2,3,1 tetrahydro 1 naphthylaminc 2 methyl-1,2,3,4-tetrahydro-l-naphthylamine (prepared by Procedure B from 2-methyl-1-tetralone) by Procedure A. The product was isolated by column chromatography to give the title compound as the free base and as a mixture of stereoisomers (white solid, mp 256-257° C.). MS(ES$^+$) m/z 278 ([M+1]$^+$, 100).

Example 19

N-(Benzimidazol-2-yl)-5,7-dimethyl-1,2,3,4-tetrahydro-1-naphthylamine

The title compound was prepared from 2-chlorobenzimidazole and 5,7-dimethyl-1,2,3,4-tetrahydro-1-naphthylamine (prepared by Procedure B from 5,7-dimethyl-1-tetralone) by Procedure A (60 min at 170° C. followed by 20 min at 200° C.). The product was purified by recrystallisation to give the title compound as the free base and as a mixture of enantiomers (white solid, mp 250-252° C.). MS(ES$^+$) m/z 292 ([M+1]$^+$, 100).

Example 20

N-(Benzimidazol-2-yl)-4-methyl-1,2,3,4-tetrahydro-1-naphthylamine

The title compound was prepared from 2-chlorobenzimidazole and 4 methyl-1,2,3,4-tetrahydro-1-naphthylamine (prepared by Procedure B from 4-methyl-1-tetralone) by Procedure A. The product was isolated by recrystallisation to give the title compound as a HCl salt and as a mixture of stereoisomers (white solid, mp 276° C.). MS(ES$^+$) m/z 278 ([M+1]$^+$, 100).

Example 21

N-[5,7-Bis(trifluoromethyl)benzimidazol-2-yl]-1,2,3,4-tetrahydro-1-naphthylamine The title compound was prepared from 3,5-bis(trifluoromethyl)-1,2-diaminobenzene and 1-isothiocyanato-1,2,3,4-tetrahydronaphthalene by Procedure D. The title compound was isolated by column chromatography as the free base and as a mixture of enantiomers (solid, dec. >240° C.). MS(ES$^+$) m/z 400 ([M+1]$^+$, 100).

Example 22

(R)-N-(5-Methylbenzimidazol-2-yl)-1,2,3,4-tetrahydro-1-naphthylamine

The title compound was prepared from 3,4-diaminotoluene and (R)-1-isothiocyanato-1,2,3,4-tetrahydronaphthalene by Procedure D. The title compound was isolated by column chromatography as the free base (off-white solid, mp 91-93° C.). MS(ES$^+$) m/z 278 ([M+1]$^+$, 100).

Example 23

(R)-N-(5,6-Dimethylbenzimidazol-2-yl)-1,2,3,4-tetrahydro-1-naphthylamine

The title compound was prepared from 4,5-dimethylphenylenediamine and (R)-l-isothiocyanato-1,2,3,4-tetrahydronaphthalene by Procedure D. The title compound was isolated by column chromatography as the free base (solid, mp 121-124° C.). MS(ES$^+$) m/z 292 ([M+1]$^+$, 100).

Example 24

N-(5-Fluorobenzimidazol-2-yl)-1,2,3,4-tetrahydro-1-naphthylamine

The title compound was prepared from 4-fluorophenylenediamine and 1-isothiocyanato-1,2,3,4-tetrahydronaphthalene by Procedure D. The title compound was isolated by column chromatography as the free base and as a mixture of enantiomers (solid, mp 220-221° C.). MS(ES$^+$) m/z 282 ([M+1]$^+$, 100).

Example 25

N-(Benzimidazol-2-yl)-7-chloro-1,2,3,4-tetrahydro-1-naphthylamine

The title compound was prepared from 2-chlorobenzimidazole and 7 chloro-1,2,3,4-tetrahydro-1-naphthylamine (prepared by Procedure B from 7-chloro-1-tetralone) by Procedure A. The product was purified by preparative LCMS to give the title compound as the free base and as a mixture of enantiomers (white solid). MS(ES±) m/z 298 ([M+1]+, 100). ¹NMR (DMSO-d6) δ 1.72-1.95 (m, 3H), 2.02-2.09 (m, 1H), 2.67-2.80 (m, 2H), 5.00 (m, 1H), 6.82-7.18 (m, 8H), 10.6 (s, 1H).

Example 26

N-(Benzimidazol-2-yl)-7-fluoro-1,2,3,4-tetrahydro-1-naphthylamine

The title compound was prepared from 2-chlorobenzimidazole and 7-fluoro-1,2,3,4-tetrahydro-1-naphthylamine (prepared by Procedure B from 7-fluoro-1-tetralone) by Procedure A. The product was purified by column chromatography to give the title compound as the free base and as a mixture of enantiomers (white solid, mp 181° C.). MS(ES+) m/z 282 ([M+1]+, 100).

The invention claimed is:

1. A 2-amino benzimidazole chemical compound of Formula I:

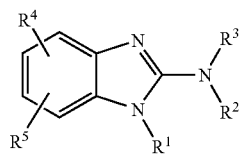

(I)

or any of its stereoisomers or any mixture of its stereoisomers, or a pharmaceutically acceptable salt thereof, wherein $R^1$ represents hydrogen or alkyl;

$R^2$ represents hydrogen, alkyl or alkoxy;

$R^3$ represents a ring-containing group selected from:

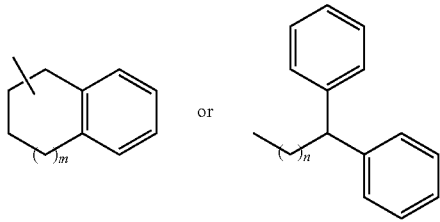

wherein m is 0, 1 or 2;

n is 0, 1, 2, 3 or 4;

and wherein the ring(s) of $R^3$ independent of each other are optionally substituted with one or more substituents independently selected from the group consisting of:

halo, trifluoromethyl, trifluoromethoxy, cyano, alkyl and alkoxy;

$R^4$ and $R^5$ independent of each other is selected from the group consisting of:

hydrogen, halo, trifluoromethyl, trifluoromethoxy, cyano, alkyl and alkoxy.

2. The chemical compound of claim 1, or any of its stereoisomers or any mixture of its stereoisomers, or a pharmaceutically acceptable salt thereof, wherein $R^1$ represents hydrogen.

3. The chemical compound of claim 1, or any of its stereoisomers or any mixture of its stereoisomers, or a pharmaceutically acceptable salt thereof, wherein $R^2$ represents hydrogen.

4. The chemical compound of claim 1, or any of its stereoisomers or any mixture of its stereoisomers, or a pharmaceutically acceptable salt thereof, wherein $R^3$ represents a 1,2,3,4-tetrahydro-naphthyl group wherein the ring is optionally substituted with one or more substituents independently selected from the group consisting of:

halo, trifluoromethyl, trifluoromethoxy, cyano, alkyl and alkoxy.

5. The chemical compound of claim 1, or any of its stereoisomers or any mixture of its stereoisomers, or a pharmaceutically acceptable salt thereof, wherein $R^3$ represents an indanyl group wherein the aromatic moiety is optionally substituted with one or more substituents independently selected from the group consisting of:

halo, trifluoromethyl, trifluoromethoxy, cyano, alkyl and alkoxy.

6. The chemical compound of claim 1, or any of its stereoisomers or any mixture of its stereoisomers, or a pharmaceutically acceptable salt thereof, wherein $R^3$ represents a 6,7,8,9-tetrahydro-5H-benzocycloheptenyl group wherein the ring is optionally substituted with one or more substituents independently selected from the group consisting of:

halo, trifluoromethyl, trifluoromethoxy, cyano, alkyl and alkoxy.

7. The chemical compound of claim 1, or any of its stereoisomers or any mixture of its stereoisomers, or a pharmaceutically acceptable salt thereof, wherein $R^3$ represents

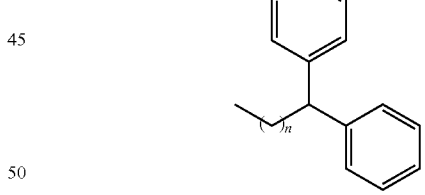

wherein the two phenyl rings independent of each other are optionally substituted with one or more substituents independently selected from the group consisting of:

halo, trifluoromethyl, trifluoromethoxy, cyano, alkyl and alkoxy.

8. The chemical compound of claim 1, or any of its stereoisomers or any mixture of its stereoisomers, or a pharmaceutically acceptable salt thereof, wherein $R^4$ and $R^5$ represent hydrogen.

9. The chemical compound of claim 1, or any of its stereoisomers or any mixture of its stereoisomers, which is N-(Benzimidazol-2-yl)-2,2-diphenylethylamine;

N-(Benzimidazol-2-yl)-2,2-bis(4-fluorophenyl)ethylamine;

N-(Benzimidazol-2-yl)-2,2-bis(4-chlorophenyl)ethylamine;
N-(Benzimidazol-2-yl)-3,3-diphenylpropylamine;
N-(Benzimidazol-2-yl)-1-indanylamine;
N-(Benzimidazol-2-yl)-2-indanylamine;
N-(Benzimidazol-2-yl)-5-fluoro-1-indanylamine;
N-(Benzimidazol-2-yl)-5-chloro-1-indanylamine;
N-(Benzimidazol-2-yl)-5-bromo-1-indanylamine;
N-(Benzimidazol-2-yl)-1,2,3,4-tetrahydro-1-naphthylamine;
N-(Benzimidazol)-2-yl)benzhydrylamine;
N-(Benzimidazol-2-yl)-4-chlorobenzhydrylamine;
N-(Benzimidazol-2-yl)-4,4'-dichlorobenzhydrylamine;
N-(Benzimidazol-2-yl)-4,4'-difluorobenzhydrylamine;
N-(Benzimidazol-2-yl)- 6,7,8,9-tetrahydro-5H-benzocyclohepten-5-ylamine;
(R)-N-(Benzimidazol-2-yl)-1,2,3,4-tetrahydro-1-naphthylamine;
(S)-N-(Benzimidazol-2-yl)-1,2,3,4-tetrahydro-1-naphthylamine;
N-(Benzimidazol-2-yl)-2-methyl-1,2,3,4-tetrahydro-l-naphthylamine; N-(Benzimidazol-2-yl)-5,7-dimethyl-1,2,3,4-tetrahydro-1-naphthylamine;
N-(Benzimidazol-2-yl)-4-methyl-1,2,3,4-tetrahydro-l-naphthylamine;
N[5,7-Bis(trifluoromethyl)benzimidazol-2-yl]-1,2,3,4-tetrahydro-1-naphthylamine;
(R)-N-(5-Methylbenzimidazol-2-yl)-1,2,3,4-tetrahydro-1-naphthylamine;
(R)-N-(5,6-Dimethylbenzimidazol-2-yl)-1,2,3,4-tetrahydro-1-naphthylamine;
N-(5-Fluorobenzimidazol-2-yl)-1,2,3,4-tetrahydro-1-naphthylamine;
N-(Benzimidazol-2-yl)-7-chloro-1,2,3,4-tetrahydro-1-naphthylamine;
N-(Benzimidazol-2-yl)-7-fluoro-1,2,3,4-tetrahydro-1-naphthylamine;
or a pharmaceutically acceptable salt thereof.

10. A pharmaceutical composition, comprising a therapeutically effective amount of a compound of claim 1, or any of its stereoisomers or any mixture of its stereoisomers, or a pharmaceutically acceptable salt thereof, together with at least one pharmaceutically acceptable carrier, excipient or diluent.

11. The chemical compound of claim 1, or any of its stereoisomers or any mixture of its stereoisomers, or a pharmaceutically acceptable salt thereof, which is
(R)-N-(Benzimidazol-2-yl)-1,2,3,4-tetrahydro-1-naphthylamine.

* * * * *